United States Patent [19]
Gupte et al.

[11] Patent Number: 4,592,754
[45] Date of Patent: Jun. 3, 1986

[54] SURGICAL PROSTHETIC VESSEL GRAFT AND CATHETER COMBINATION AND METHOD

[76] Inventors: Pradeep M. Gupte, 7 Victoria Dr., Suffern, N.Y. 10901; Ravi K. Sundaram, 2A Beechwood Hall, Westchester County Medical Center, Valhalla, N.Y. 10595

[21] Appl. No.: 530,727

[22] Filed: Sep. 9, 1983

[51] Int. Cl.⁴ .............................................. A61F 2/06
[52] U.S. Cl. .................... 623/1; 128/334 R; 604/9
[58] Field of Search ............... 128/334 R, 334 C, 325; 604/8–10, 101; 3/1.4, 1

[56] References Cited

U.S. PATENT DOCUMENTS 3,435,824 4/1969 Gamponia ....................... 604/101 X
3,657,744 4/1972 Ersek ........................... 128/334 R X
4,230,119 10/1980 Blum ............................. 604/101 X

FOREIGN PATENT DOCUMENTS 2805749 8/1978 Fed. Rep. of Germany ........... 3/1.4

Primary Examiner—Michael H. Thaler
Attorney, Agent, or Firm—Curtis Ailes

[57] ABSTRACT

The combination comprises a prosthetic vessel graft having a limited wall opening and a catheter device having at least two interconnected tubular arms extending through the wall opening and through the interior of the graft and through opposite ends of the graft. The end of each arm includes an inflatable balloon collar for secure connection to the interior of a vessel to be repaired by inflation of the balloon collar.

In the method, the ends of the catheter arms are inserted and secured through small incisions in a vessel on either side of a section to be replaced by the graft. The section is removed, the graft is attached, the catheter is removed through the graft wall opening, and the wall opening is then closed.

12 Claims, 8 Drawing Figures

SURGICAL PROSTHETIC VESSEL GRAFT AND CATHETER COMBINATION AND METHOD

BACKGROUND OF THE INVENTION

The present invention relates particularly to a surgical prosthetic vessel graft and catheter combination, and to a method of installing such a graft. The combination and the method are particularly useful for the repair of blood vessels, and particularly for major arterial vessels such as the aorta.

A relatively serious and fairly common health problem involves the development of diseased conditions in major arteries of the body, particularly the aorta. Such problems frequently take the form of a weakened section of the artery and the development of an aneurysm (a localized abnormal dilation). The weakness which results in the aneurysm is frequently indicative of a serious risk of arterial hemorrhage.

One preferred treatment for such a condition is the surgical removal and replacement of the section of the vessel containing the aneurysm with a graft prosthetic vessel. This has become a fairly common procedure. However, there are serious technical problems with the procedure as commonly practiced. One requirement for the operation is that some occlusion means must be provided for preventing loss of blood during the removal of the defective vessel section and the substitution of the graft. The most obvious procedure is to simply use clamps to occlude the vessel on both sides of the graft site before the defective section is removed and while the graft is being attached, and to then remove the clamps after the graft has been secured.

This procedure involves serious difficulties, and risk of damage to the adjacent portions of the vessels which are clamped, particularly in cases of severe arteriosclerotic vessels. In a patient who has developed an aneurysm, the adjacent vessel sections are often weak and arteriosclerotic, and may actually be cracked or damaged by the occlusive clamps. Also, the use of the clamps may dislodge plaques which are common within the arteries of patients having arteriosclerosis, increasing the risk of forming an obstruction. The risk of damage to the artery from clamping is especially serious if calcification has developed in the interior of the artery. In such an instance, placing the clamp on the vessel may cause the calcium to break up, risking rupture of the vessel, or damage, from the broken calcium, and causing the broken calcium particles to tend to move in the artery, and to possibly act as an occluding embolus.

In order to avoid the problems associated with clamping, it has previously been proposed to provide an occluding balloon catheter. Such a catheter, and the use of such a catheter for vascular surgical repairs is disclosed in U.S. Pat. No. 3,833,003 issued on Sept. 3, 1974 to Alfred Taricco for an "INTRAVASCULAR OCCLUDING CATHETER". When such a device is used, it is inserted through an incision in the wall of the vessel, preferably on the upstream side of the defect, and then a balloon collar on the end of the catheter is inflated through the catheter tube so as to occlude the vessel to prevent bleeding during repair. Preferably, a second catheter is also inserted and inflated in the vessel on the opposite side of the defect to be repaired. The balloon catheter has the major advantage that the clamp formed by the balloon is form fitting to the internal shape of the vessel, and is gentle yet firm, and does not have nearly as much potential as a clamp for damage to the vessel wall. After the repair is completed, the balloons of each of the balloon catheters are deflated, and each catheter is removed through the incision where it was inserted. Each of the incisions must then be closed. These last mentioned incisions, and the necessity for closing these incisions in the vessel walls presents a disadvantage which it would be very desirable to overcome.

Accordingly, it is one object of the present invention to provide, in the instance where the repair consists of the insertion of a prosthetic vessel graft, a combination device and method which avoids the necessity for sewing up two incisions in the wall of the vessel where the catheters have been inserted.

It has also been recognized that, in addition to avoiding loss of blood during vascular repairs, it is very desirable to provide for a shunt flow of blood around the diseased vessel portion which is to be repaired or replaced in order to minimize trauma to the parts of the body which would normally be provided with blood through the diseased portion. This problem has been addressed previously by shunt catheters which include balloon collar means for attachment. Such devices are disclosed, for instance, in U.S. Pat. No. 3,435,824 issued Apr. 1, 1969 to Herminio Gamponia for a "SURGICAL APPARATUS AND RELATED PROCESS" and also in U.S. Pat. No. 3,516,408 issued June 23, 1970, to Vincent Montanti for an "ARTERIAL shunt".

In the devices illustrated in each of these patents, a shunt tube is provided with a balloon collar at each end. The ends are inserted through incisions in the artery on opposite sides of the defect, and inflated to isolate the defect and to permit the passage of blood through the shunt. After the repair has been completed, the balloons are deflated and the ends of the tubes are removed through the incisions through which they were inserted and the incisions are sewed up. Again, the repair of these incisions in the walls of the vessel being repaired represent a serious disadvantage, particularly in a patient whose vessels are weak and diseased.

Accordingly, it is another object of the present invention to provide for a shunt catheter and prosthetic graft combination and method where the necessity for repairing incisions made for insertion of the ends of the catheter in the walls of the vessel is avoided.

Another problem in conjunction with the use of a shunt catheter of the type referred to immediately above is that the flow of blood through the shunt is not controllable. Thus, during the interval when the upstream end of the shunt is attached, and the downstream end is not yet attached, blood can be lost through the shunt device itself. Furthermore, there may be a need for arresting blood flow through the shunt device while further repairs downstream of the shunt are made.

Accordingly, it is another object of the invention to provide for a shunt device combination and method in which blood flow through the shunt may be controlled, at will.

One of the portions of the vascular system which often requires repair is at the bifurcation of the aorta at the intersection with the iliac arteries. Furthermore, in the present practice it is common to provide a prosthetic vessel graft for that bifurcated portion of the aorta artery. In such an operation, the prevention of blood loss and the provision of the shunt function is much more complicated. The above mentioned Gamponia patent disclosed a bifurcated bipass device, which presumably might be suitable for repair of the bifurcated portion of the aorta. However, the use of such a device would involve the necessity for repairing three separate incisions for the insertion of the three separate ends of the shunt, after the operation, and no means is provided for the prevention of loss of blood when using the Gamponia device after one or two of the device ends have been attached, and before the last one is attached and secured by its balloon collar.

Accordingly, it is another object of the invention to provide a device combination and a method which are particularly useful for the installation of a prosthetic graft to replace the bifurcated portion of the aorta.

Further objects and advantages of the invention will be apparent from the following description and the accompanying drawings.

SUMMARY OF THE INVENTION

In carrying out the invention there is provided a surgical prosthetic vessel graft and catheter combination comprising a prosthetic vessel graft having a limited opening in the wall thereof, a catheter device having at least two interconnected tubular arms extending through said graft wall opening and extending through the interior of said graft and through opposite ends of said graft, the end of each of said arms including an inflatable balloon collar for secure connection to the interior of a vessel to be repaired by inflation of said balloon collar, said catheter device including individual inflation tubes for each of said balloon collars extending through said graft wall opening to said respective balloon collars.

In another aspect of the invention, the invention may be carried out by a combination as described in the preceding paragraph, and wherein said interconnected tubular arms include interconnected inner passages for the passage of a body fluid such as blood for the purpose of providing a shunt connection for the transmission of the body fluid through said catheter to thereby shunt a section of a vessel to be repaired during that repair.

In still another aspect of the invention, there may be provided a surgical method for the installation of a prosthetic vessel graft within the body of a patient to replace a diseased section of vessel comprising the steps of providing a limited opening in the wall of the prosthetic vessel graft, inserting the ends of the individual arms of a catheter having at least two arms through said opening, threading said respective arms through the interior of said graft in opposite directions so that said arms protrude through the respective ends of said graft, said catheter being provided with a balloon collar at the end of each of said arms with inflation tubes extending to each of the collars through the opening in the wall of the graft, the method further including the steps of making a small incision in the wall of the vessel to which the graft is to be attached on one side of the diseased section of the vessel to be replaced, inserting the end of one of said arms of the catheter through the last mentioned incision and extending away from the section to be replaced, and then inflating the associated collar to form a seal with the interior of the vessel, making a small incision in the wall of the vessel on the other side of the section of vessel to be replaced inserting the other arm of said catheter through the last-mentioned incision and extending away from the section to be replaced and then inflating the associated collar to form a seal with the interior or of the vessel, then removing the diseased section of vessel to be replaced by the graft by cutting at positions at or beyond the positions of the last named incisions in the wall of the vessel so as to effectively remove those incisions, stitching the respective ends of the graft to the cut-away ends of the vessel, deflating the balloon collars at the ends of said arms, removing the catheter arms from the combination of the repaired vessel and the graft through the opening in the wall of said graft, and then stitching up the opening in the graft.

DESCRIPTION OF PREFERRED EMBODIMENTS

Figure 1:
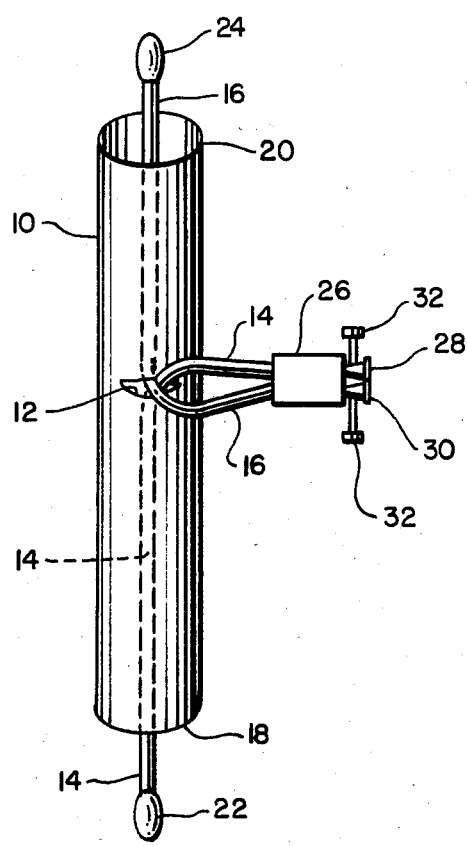
FIG. 1 is a perspective side view of one embodiment of the combination of the invention.

Referring more particularly to the drawings, FIG. 1 illustrates one embodiment of the surgical prosthetic vessel graft and catheter combination of the present invention. It includes a prosthetic vessel graft 10 having a limited opening 12 in the wall thereof. The combination also includes a catheter device having two interconnected tubular arms 14 and 16 extending through the wall opening 12 and extending through the interior of the graft 10 and through the opposite ends 18 and 20 of the graft 10. At the ends of each of the respective arms 14 and 16 there are inflatable balloon collars 22 and 24 for the purpose of establishing secure connections to the interior of a vessel to be repaired. Each arm of the catheter is inserted through an incision in the vessel, and the balloon collar is then inflated. The inflation not only establishes a secure connection to the interior of the vessel, but also closes off the vessel to prevent bleeding. Each arm 14 and 16 includes an individual inflation tube for each of the balloon collars. In the embodiment of FIG. 1, those inflation tubes may actually comprise the arms 14 and 16, or may extend through the interior of those arms.

The arms 14 and 16 of the catheter are preferably composed of substantially circular tubes of a flexible synthetic resin material. Preferably they are a clear plastic.

The ends of the arms 14 and 16 are connected together physically by a common collar fitting 26, and each arm is equipped at the end protruding through the fitting 26 with a connector for connection of a syringe, as indicated respectively at 28 and 30. The syringes may be used for the purpose of introducing fluid through the catheter arms to the ballon collars 22 and 24. Each of the syringe fittings 28 and 30 preferably includes a manually operated valve, as indicated by the valve handles 32, in order to control the release of fluid from the balloon collars 22 and 24 after the fluids once injected into those collars. An aqueous fluid is preferred for inflating the collars, preferably a saline solution.

The method, according to the invention, is described in detail below with particular reference to FIGS. 6, 7, and 8. However, the method may be briefly described in relation to FIG. 1, as follows: when the graft 10 is to be installed in substitution for a diseased section of vessel, small incisions are made at each end of the vessel section which is to be replaced, and the ends of the arms 14 and 16, carrying the balloon collars 22 and 24, are inserted into the vessel through those incisions and are positioned beyond the incisions and beyond the boundaries of the vessel section which is to be replaced. The balloon collars are then inflated to attach the catheters within the vessel walls and to prevent the loss of blood when the vessel section to be replaced is removed. The vessel section to be replaced is then cut away, including the incisions which were made for the insertion of the catheter arms, and the ends of the graft 10 are attached to the cut ends of the vessel. The balloon collars 22 and 24 are then deflated, and the arms of the catheter are removed through the opening 12 in the wall of the graft. The opening 12 is then permanently closed, and the method is thus completed.

The opening 12 may be equipped with a surgical zipper (not shown) for quick closure. In any case, the opening 12 is preferably finished or "bound" at the edges to prevent any unravelling, and to provide a more sturdy edge for stitching or stapling shut.

Figure 2:
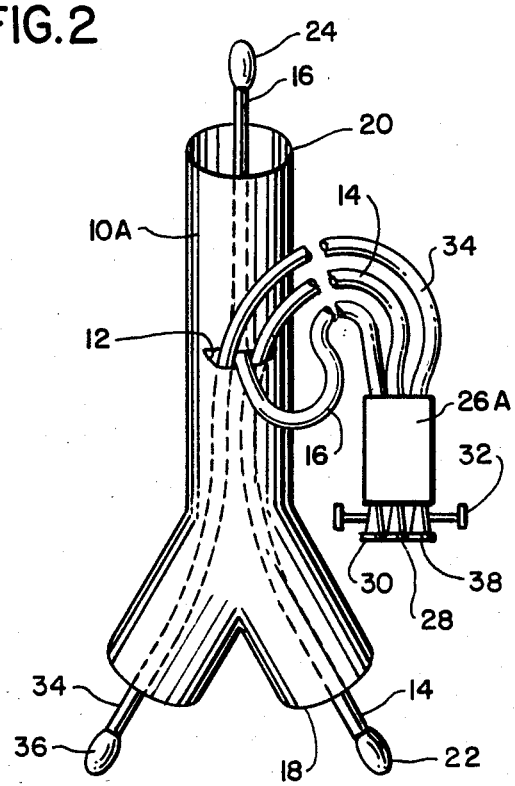
FIG. 2 is a modification of the embodiment of FIG. 1 to be used for replacement of a bifurcated portion of a vessel.

FIG. 2 is substantially the same as FIG. 1, except that the graft 10A illustrated in FIG. 2 is a "Y" shaped graft which is intended for replacement of a "Y" section of vessel such as the junction of the aorta with the iliac arteries. Also, in the embodiment of FIG. 2, a third arm 34 is provided for the catheter which includes a balloon collar 36. Also, the arm 34 is terminated at the collar 26A with a valved fitting 38 for a syringe.

Figure 3:
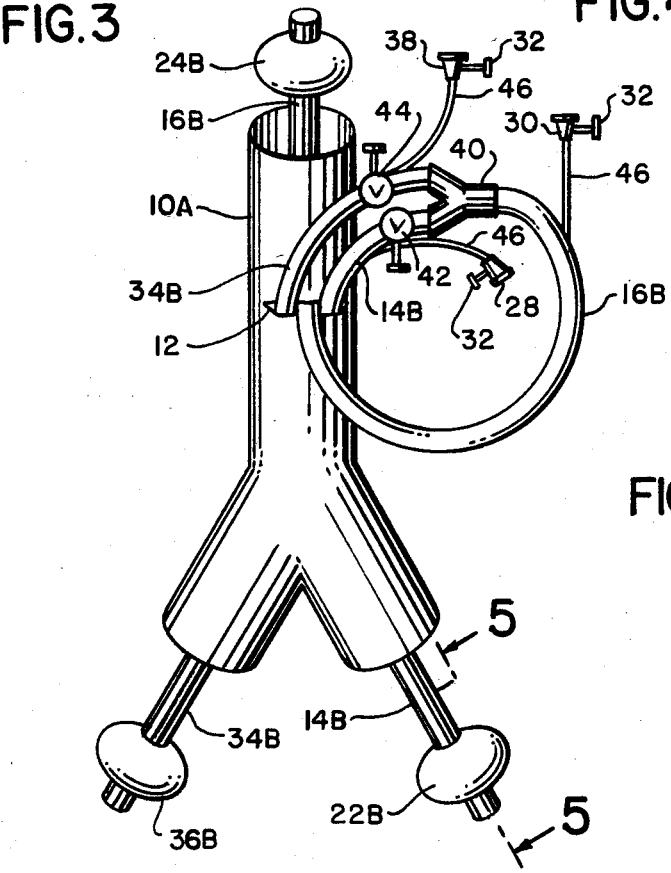
FIG. 3 is a modification of the embodiment of FIG. 2 in which provision is made for shunt connections for carrying body fluids through the catheter.

FIG. 3 illustrates a modification of the embodiment of FIG. 2 in which each of the arms of the catheter includes an interior passage, and those interior passages of the arms are interconnected to provide for the shunt of body fluids through the catheter during the surgical procedure for the insertion of the graft. Bypassing or shunting the body fluids around the graft is of great benefit since it reduces the trauma otherwise caused by temporary obstruction of the passage of body fluids during the surgical procedure. (The terms "shunt" and "bypass" are used interchangeably in this specification.) Thus, particularly in the case of blood vessel grafts, blood circulation is maintained during the surgical procedure, thus avoiding the risk of possible damage due to the temporary interruption of blood supply. This also reduces the time pressure on the surgeon to complete the procedure to restore blood circulation.

Parts of FIG. 3 which correspond exactly with parts of FIG. 2 are given corresponding numerical designations. Those parts which have similar, but not identical, counterparts in FIG. 2 are given the same designation with the letter suffix "B".

The inner ends of the arms 14B, 16B, and 34B are interconnected by a "Y" fitting 40. Each of the arms 14B and 34B preferably also include a manually operable valve, as respectively shown at 42 and 44. These valves can be used to provide for complete occlusion (when both are closed) as the ends of the catheter arms are initially installed. The valves may then be selectively opened to provide shunt flow.

In each of the embodiments of FIGS. 1, 2, and 3, it can be said that the interconnected portions of the arms of the catheter form a loop with the opposite ends of the loop extending through the graft wall opening 12 in opposite directions along the graft 10 or 10A. Thus, the arm 16B extends through the opening 12 and upwardly through the graft 10A, while the arms 14B and 34B extend through the graft opening 12 and in a downward direction through the graft 10A.

Figure 4:
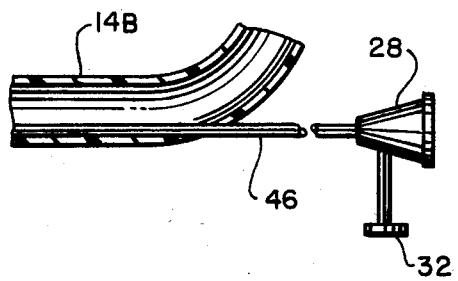
FIG. 4 is a detail of a portion of the embodiment of FIG. 3 showing the arrangement for the supply of fluid for inflation of a balloon collar which forms a part of the catheter.

In the embodiment of FIG. 3, separate inflation tubes are provided for the balloon collars 22B, 24B, and 36B. Those tubes extend from the syringe fittings 28, 30, and 38, as shown at 46, and into the associated arms 14B, 16B and 34B of the catheter. The inflation tubes 46 may preferably be molded into the inner wall of the tube forming each of the various arms. An enlarged detail of this is illustrated in FIG. 4, which shows the entrance of one of the tubes into an associated arm.

Figure 5:
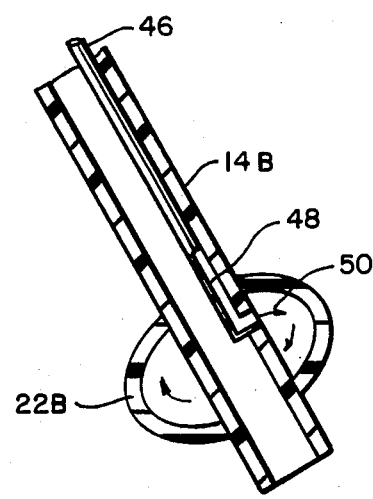
FIG. 5 is an enlarged detail view, in section, of an end portion of one of the catheter arms, showing the arrangment of an inflatable balloon collar.

FIG. 5 is an enlarged sectional view, taken at section 5—5 in FIG. 3, illustrating the outer end of the arm 14B, and showing how the inflation tube 46 is arranged inside the tube 14B. As shown in that drawing, the tube 46 is illustrated in section at its terminal end, as indicated at 48, and a suitable opening from the end of the tube 46 is provided through the wall of the arm 14B and into the interior of the balloon collar 22B, as illustrated at 50.

It will be understood that, while the collars 22B, 24B, and 36B are shown inflated in FIG. 3 and FIG. 5 for illustrative purposes, those inflatable collars are not normally inflated until the associated arms are inserted into the vessels in which they are to be attached.

Figure 6:
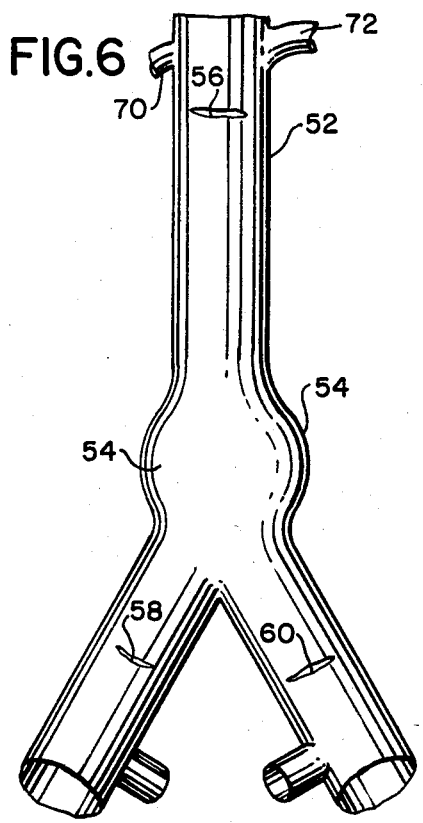
FIG. 6 illustrates the portion of the vessel structure of a patient which is to be replaced by the prosthetic vessel graft, and showing the incisions which must be made for the initial installation of the combination apparatus in the practice of the method of the present invention.
Figure 8:
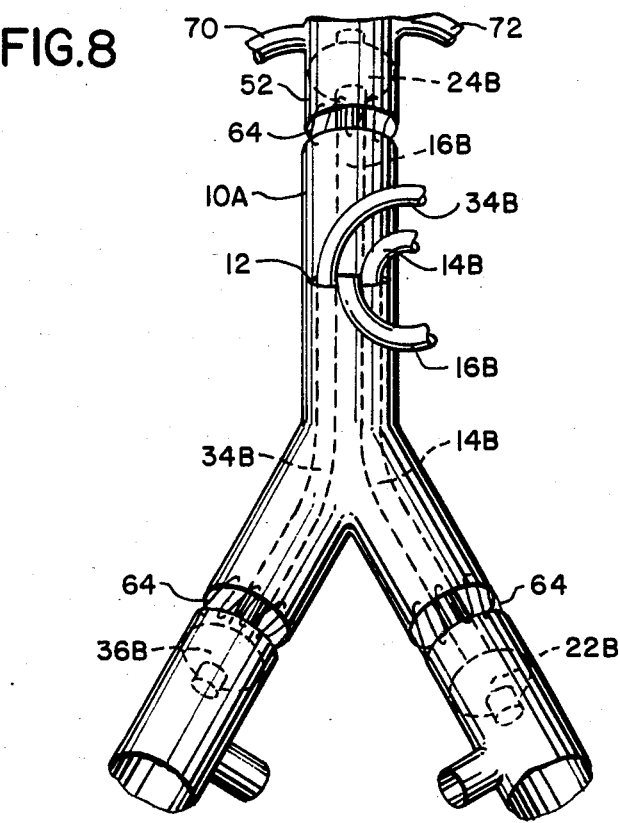
FIG. 8 illustrates how the prosthetic vessel graft is finally attached to the remaining vessels of the patient after the removal of the diseased section in the practice of the method of the invention.
Figure 7:
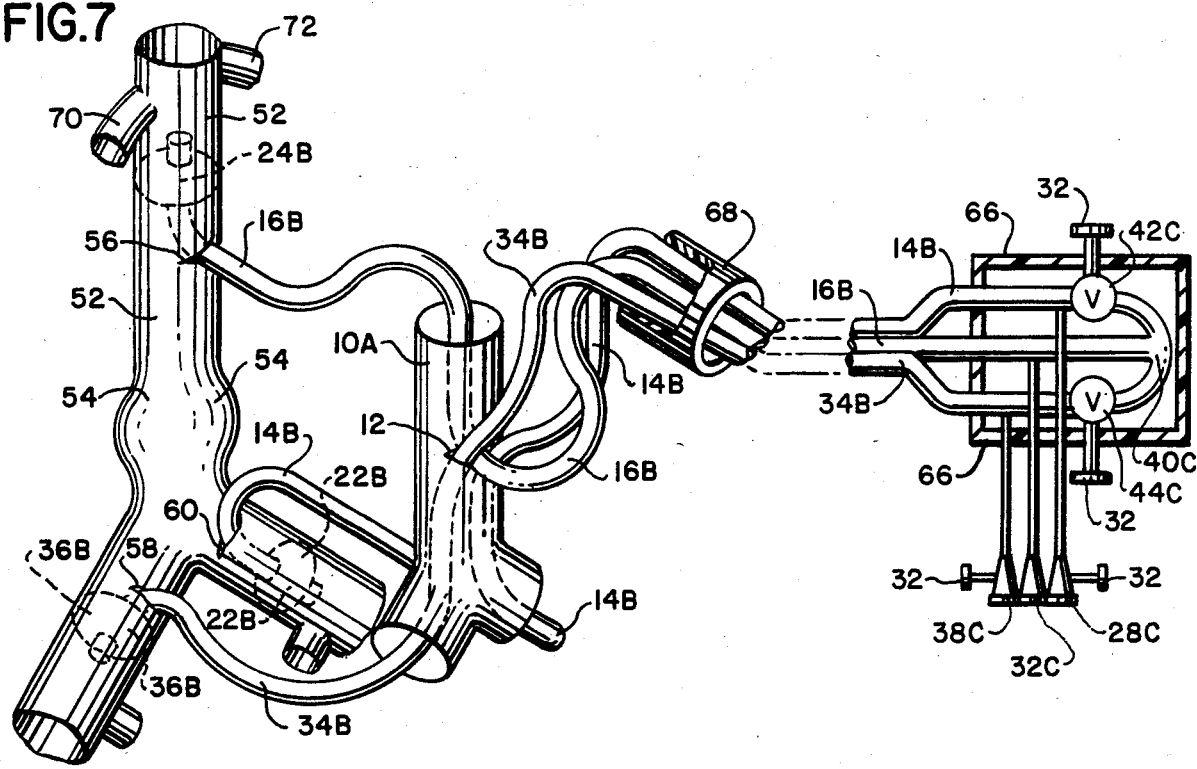
FIG. 7 illustrates how the apparatus combination of the present invention is initially attached in the vessel section of FIG. 6 in the practice of the method of the present invention, and also showing apparatus modifications.

FIGS. 6, 7, and 8, taken together, illustrate the method of the invention. Also, FIG. 7 illustrates a modification of the structure of the embodiment of FIG. 3 which relates primarily to the arrangement of the arms of the catheter and their mode of mutual attachment.

Referring particularly to FIG. 6, there is shown a partial view of a bifurcated portion 52 of the arterial system of a patient which requires replacement by a prosthetic vessel graft by reason of the development of an aneurysm 54. For instance, the bifurcated portion 52 may represent the lower end of the aorta at the juncture with the two iliac arteries. As a first step in the procedure, incisions are made at 56, 58, and 60 for the insertion of the outer ends of the catheter arms. The incisions 56, 58, 60 are respectively made at about the locations of the ends of the section of vessel which is to be replaced. While all three of the incisions 56, 58 and 60 are illustrated in FIG. 6, in the preferred method of the invention only one of these incisions will be made at a time. Then the associated catheter arm is inserted and the associated balloon collar is inflated in order to prevent bleeding through that incision.

Referring more particularly to FIG. 7, in the preferred method, the incision 56 in the aorta is first made and the arm 16B is then inserted through that incision 56, and extended upstream of the incision 56. The balloon collar 24B is then inflated by the injection of fluid into that collar. The shunt flow valves 42 and 44 are both initially closed. Thus, the inflation of the balloon collar 24B provides a full occlusion of the aorta at that point and prevents any continuation of blood loss through the incision 56.

Next, one of the iliac incisions is made, such as at 58, and the catheter arm 34B is inserted through that incision and the associated balloon collar 36B is inflated. The position of the inflated balloon collar 36B is downstream, beyond the incision 58. The valve 44C is then opened to permit the resumption of circulation to the iliac artery associated with catheter arm 34B. The incision 60 is next made and the arm 14B is inserted and the collar 22B is inflated. The other valve 42C is then opened, permitting bypass flow to the other iliac artery.

As soon as all three of the arms 14B, 16B, and 34B of the catheter are firmly secured, and shunt flow is established, the next step in the method is to enlarge each of the incisions 56, 58, and 60, or to cut beyond those incisions to detach each of the respective ends of the vessel section 52 to be removed. The prosthetic vessel graft 10A is then moved into position to be sewn into place, as illustrated in FIG. 8.

FIG. 8 shows the prosthetic vessel graft in place and ready for the respective ends of the graft to be sewn to the associated cut vessel ends of the patient.

The sutures used to close up the connections between the ends of the graft and the vessels of the patient are schematically indicated at 64. After these three attachments are completed, the shunt control valves 42 and 44 may be closed, the balloon collars are deflated one at a time, and the associated arms are carefully removed through the opening 12 in the graft 10A. After all of them have been removed, the opening 12 is closed and the repair of the vessels is thus completed. Preferably, the shunt valves 42 and 44 are closed one at a time, and the associated downstream arm is then removed. Thus, as the first downstream arm is removed, shunt flow is continued through the other downstream arm. The second valve may then be closed and the second downstream arm is removed, after which the upstream arm is removed and the opening 12 in the graft is closed.

The opening 12 may be sewn shut, or may be closed by a surgical zipper (not shown) which is built into the graft.

FIG. 7 not only discloses an intermediate step in the method, but also discloses a preferred modification of the embodiment of FIG. 3 in which the Y connection 40, the valves 42 syringe are combined in a single enclosure 66. The components just listed, since they are somewhat different from those shown in FIG. 3, bear the same numbers with the suffix letter C. The organization of all of these components into a single enclosure 66 makes the assembly of the catheter much easier to handle. Furthermore, the arms 14B, 16B and 34B are made so that they are long enough so that the box 66 and all of the components enclosed therein can be positioned outside of the field of the surgical operation while it is underway, so that those components do not interfere wth the performance of the operation.

In order to keep the arms 14B, 16B, and 34B better organized, there is preferably provided a sleeve 68 which has a snug fit around the three arms 14B, 16B and 34B, and which, during the operation, can be slid up close to the opening 12 in the graft 10A so as to keep the arms in a unified bundle, which again helps to avoid interference with the surgical operation, keeping the field clear and unobstructed. If desired, several sleeves 68 may be provided for positioning along the full length of the arms 14B, 16B, and 34B between the box 66 and the opening 12.

Up to this point, the description of the invention has been directed to arrangements in which the catheter has either two or three arms, and the prosthetic vessel graft has either two or three terminal ends to be attached to the corresponding vessel ends of the patient. However, it will be understood that the principles of the invention are applicable to situations involving additional arterial branches, and in which the prosthetic vessel graft may replace a natural part of the arterial system having more than three elements or branches.

For instance, the renal arteries are illustrated at 70 and 72 in FIGS. 6, 7, and 8. The renal arteries branch off from the aorta 52 to supply the kidneys. It is very important that circulation be maintained to the kidneys in order to maintain the vital kidney function. The above description, in relation to FIGS. 6, 7, and 8, has been restricted to the problem of an aneurism or other defect occuring in the section of the aorta below the renal artery branches. However, if the diseased part of the aorta extends above the renal branches 70 and 72, or so close to those brances that the balloon cuff 24B must be placed above the renal artery branches 70 and 72, the circulation will be cut off to the renal arteries. In order to avoid that problem, the catheter of the invention may be provided with one or more additional branches which can be inserted through incisions in the renal arteries in order to maintain circulation to those arteries during the surgical procedure. Such catheter branches may not require balloon cuffs, particularly if the catheter tube itself closely approximates the interior dimension of the renal artery.

Accordingly, it is contemplated that the invention may be applied to situations involving catheters having more than three arms, and prosthetic vessel grafts having a greater number than the three connections illustrated.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

We claim:

1. A surgical prosthetic vessel graft and catheter combination comprising a prosthetic vessel graft having a limited opening in the wall thereof, a catheter device having at least two interconnected tubular arms extending through said graft wall opening and extending through the interior of said graft and through opposite ends of said graft, the end of each of said arms including an inflatable balloon collar for secure connection to the interior of a vessel to be repaired by inflation of said balloon collar, said catheter device including individual inflation tubes for each of said balloon collars extending through said graft wall opening to said respective balloon collars and said inflation tubes for said balloon collars being combined with the respective arms of said catheter device, said interconnected tubular arms including interconnected inner passages for the passage of a body fluid such as blood for the purpose of providing a shunt connection for the transmission of the body fluid through said catheter to thereby shunt a section of a vessel to be repaired during that repair.

2. A combination as claimed in claim 1 wherein said arms are substantially circular in cross-section and said inflation tubes are confined within the circular cross-section.

3. A combination as claimed in claim 1 wherein there are provided three arms.

4. A combination as claimed in claim 1 wherein said catheter includes a valve means for selectively closing off circulation of a body fluid through at least one of said arms.

5. A surgical prosthetic vessel graft and catheter combination comprising a prosthetic vessel graft having a limited opening in the wall thereof, a catheter device having at least two interconnected tubular arms extending through said graft wall opening and extending through the interior of said graft and through opposite ends of said graft, the end of each of said arms including an inflatable balloon collar for secure connection to the interior of a vessel to be repaired by inflation of said ballon collar, said catheter device including individual inflation tubes for each of said balloon collars extending through said graft wall opening to said respective balloon collars and said inflation tubes for said balloon collars being combined with the respective arms of said catheter device, the interconnected portions of said arms forming a loop with the opposite ends of said loop extending through said graft wall opening in opposite directions along said graft.

6. A surgical prosthetic vessel graft and catheter combination comprising a prosthetic vessel graft having a limited opening in the wall thereof, a catheter device having at least two interconnected tubular arms extending through said graft wall opening and extending through the interior of said graft and through opposite ends of said graft, the end of each of said arms including an inflatable balloon collar for secure connection to the interior of a vessel to be repaired by inflation of said balloon collar, said catheter device including individual inflation tubes for each of said balloon collars extending through said graft wall opening to said respective balloon collars and said inflation tubes for said balloon collars being combined with the respective arms of said catheter device, said graft being a bifurcated graft and said catheter including three arms, the interconnections between said arms being at a position common to all three of said arms and said common interconnection comprising a part of said loop which is outside said graft opening, two of said arms extending through said graft opening and along the interior of said graft in the direction towards the bifurcated end and respectively through the bifurcated ends, and the other arm extending through said graft opening and along the interior of said graft in the other direction.

7. A combination as claimed in claim 6 wherein said interconnected tubular arms include interconnected inner passages for the passage of a body fluid such as blood for the purpose of providing a shunt connection for the transmission of the body fluid through said catheter to thereby shunt a section of a vessel to be repaired during that repair.

8. A combination as claimed in claim 7 wherein said catheter includes a valve means for selectively closing off circulation of a body fluid through at least one of said arms.

9. A combination as claimd in claim 8 wherein said valve means includes individual valve devices arranged in at least the two arms extending through said bifurcated ends of said graft for individually selectively controlling the flow of body fluid through those respective arms.

10. A surgical method for the installation of a prosthetic vessel graft within the body of a patient to replace a diseased section of vessel comprising the steps of providing a limited opening in the wall of the prosthetic vessel graft, inserting the ends of the individual arms of a catheter having at least two arms through said opening, threading said respective arms through the interior of said graft in opposite directions so that said arms protrude through the respective ends of said graft, said catheter being provided with a balloon collar at the end of each of said arms with inflation tubes extending to each of the collars through the opening in the wall of the graft, the method further including the steps of making a small incision in the wall of the vessel to which the graft is to be attached on one side of the diseased section of the vessel to be replaced, inserting the end of one of said arms of the catheter through the last mentioned incision and extending away from the section to be replaced, and then inflating the associated collar to form a seal with the interior of the vessel, making a small incision in the wall of the vessel on the other side of the section of vessel to be replaced inserting the other arm of said catheter through the last-mentioned incision and extending away from the section to be replaced and then inflating the associated collar to form a seal with the interior inflating the associated collar to form a seal with the interior of the vessel, then removing the diseased section of vessel to be replaced by the graft by cutting at positions at or beyond the positions of the last named incisions in the wall of the vessel so as to effectively remove those incisions, stitching the respective ends of the graft to the cut-away ends of the vessel, deflating the balloon collars at the ends of said arms, removing the catheter arms from the combination of the repaired vessel and the graft through the opening in the wall of said graft, and then stiching up the opening in the graft.

11. A method as claimed in claim 10 wherein the catheter includes interconnected inner passages for the passage of a body fluid such as blood for the purpose of providing a shunt connection for the transmission of the body fluid through the catheter during the practice of the method to thereby shunt a section of a vessel to be repaired during that repair, the catheter also including a valve means for selectively closing off circulation of body fluid through at least one of said arms, and the method including the additional steps of closing the valve means prior to the insertion of the ends of the arms of the catheter through the incisions in the walls of the vessel in which the section is to be replaced, and then opening the valve means after the collars on the arms have been inflated to form seals with the interior of the vessel.

12. A method as claimed in claim 11 wherein the prosthetic vessel graft is a bifurcated graft and the associated catheter has three arms corresponding to the three arms of the bifurcated graft and the catheter includes two valves for controlling the flow of body fluid through each of the arms and wherein the method includes the additional steps of closing both of said valves prior to the insertion and attachment of the ends of the arms of the catheter within the vessels of the patient, and then opening one of said valves to permit flow as soon as the two arms of the catheter controlled by that valve have been secured within the vessels of the patient, and then opening the second one of the valves after the third arm of the catheter is secured within the vessels of the patient.

* * * * *

UNITED STATES PATENT AND TRADEMARK OFFICE
CERTIFICATE OF CORRECTION

PATENT NO. : 4,592,754
DATED : June 3, 1986
INVENTOR(S) : Pradeep M. Gupte, Ravi K. Sundaram It is certified that error appears in the above-identified patent and that said Letters Patent are hereby corrected as shown below:

Column 3, line 67, "interior or of" should read --interior of--.

Column 5, line 13, "after the fluids" should read --after the fluid is--.

Column 7, line 52, before "syringe", insert --and 44, and the connections 28, 32, and 38 for the inflation--.

Column 7, line 63, "wth" should read --with--.

Column 8, line 27, "brances" should read --branches--.

Column 9, line 65, "claimd" should read --claimed--.

Column 10, line 27, "inflating the associated collar to form a seal with the interior" should be deleted.

Signed and Sealed this

Sixteenth Day of September 1986

[SEAL]

Attest:

DONALD J. QUIGG

Attesting Officer     Commissioner of Patents and Trademarks